(12) United States Patent
Trask et al.

(10) Patent No.: US 7,150,970 B2
(45) Date of Patent: Dec. 19, 2006

(54) METHODS OF INHIBITING VEGF-C

(75) Inventors: Douglas K. Trask, Coralville, IA (US); Jonathan Bock, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 11/194,276

(22) Filed: Aug. 1, 2005

(65) Prior Publication Data

US 2006/0025370 A1 Feb. 2, 2006

Related U.S. Application Data

(60) Provisional application No. 60/598,003, filed on Aug. 2, 2004.

(51) Int. Cl.
*C12Q 1/68* (2006.01)
*A61K 48/00* (2006.01)
*C07H 21/04* (2006.01)

(52) U.S. Cl. .......................... 435/6; 435/325; 435/375; 536/24.5; 536/23.1; 514/44

(58) Field of Classification Search .................. 435/6, 435/4, 325, 375; 536/24.5, 23.1; 514/44; 424/145.1
See application file for complete search history.

(56) References Cited

FOREIGN PATENT DOCUMENTS

EP 1 382 679 1/2004

OTHER PUBLICATIONS

International Search Report for PCT Application Serial No. PCT/US2005/027278, mailed Dec. 7, 2005.
Database EMBL May 24, 1997, Hillier et al., "zw46b06.r1 Soares total fetus Nb2HF8_9w", XP002353389 retrieved from EBI Database accession No. AA425486.
Database EMBL Mar. 3, 2004, Lee, J. and Wood, W.: "Sequence 8 from Patent EP 1382679" XP002353390 retrieved from EBI Database accession No. CQ764840.

*Primary Examiner*—James Schultz
*Assistant Examiner*—Dana Shin
(74) *Attorney, Agent, or Firm*—Viksnins Harris & Padys PLLP

(57) ABSTRACT

The present invention provides RNA molecules (e.g., antisense, RNAi, or siRNA) specific for VEGF-C, and further provides methods of reducing expression of VEGF-C in cells (e.g., cancer cells).

19 Claims, 1 Drawing Sheet

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 1
aagatctgga ggagcagtta c                                              21

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 2

```
aaaggaggct ggcaacataa c                                              21

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 3
aacctccatg ttgtgtccgt c                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 4
aagacctgcc ccaccaatta c                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA oligonucleotide transcribing siRNA

<400> SEQUENCE: 5
aagacctgcc ccaccaatta c                                              21
```

METHODS OF INHIBITING VEGF-C

CLAIM OF PRIORITY

This patent application claims priority to U.S. application Ser. No. 60/598,003 filed on Aug. 2, 2004. The instant application claims the benefit of the listed application, which is hereby incorporated by reference herein in its entirety.

TECHNICAL FIELD

This invention relates to siRNA molecules, and more particularly to VEGF-C siRNA molecules.

BACKGROUND

Vascular endothelial growth factor C (VEGF-C; also known as vascular permeability factor) is a member of the signaling growth factor family. VEGF-C is a growth factor active in angiogenesis and endothelial cell growth, and stimulates their proliferation and migration. VEGF-C also has effects on the permeability of blood vessels. VEGF-C may function in angiogenesis of the venous and lymphatic vascular systems during embryogenesis, and also in the maintenance of differentiated lymphatic endothelium in adults. VEGF-C generally has several cysteine-rich motifs, and usually is about 47 kDa. VEGF-C is expressed in the spleen, lymph node, thymus, appendix, bone marrow, heart, placenta, ovary, skeletal muscle, prostate, testis, colon and small intestine, fetal liver, fetal lung, and fetal kidney.

SUMMARY

The present invention provides RNA molecules (e.g., antisense, RNAi, or siRNA) specific for VEGF-C, and further provides methods of reducing expression of VEGF-C in a cell (e.g., a cancer cell).

In one aspect, the invention provides an isolated nucleic acid molecule having a first portion. Generally, the first portion is no more than 30 nucleotides in length, and includes the sequence 5'-AAG ATC TGG AGG AGC AGT TAC-3' (SEQ ID NO:1), 5'-AAA GGA GGC TGG CAA CAT AAC-3' (SEQ ID NO:2), 5'-AAC CTC CAT GTT GTG TCC GTC-3' (SEQ ID NO:3), 5'-AAG ACC TGC CCC ACC AAT TAC-3' (SEQ ID NO:4), or 5'-AAG AAG TGT GTC GTT GTG TCC-3' (SEQ ID NO:5).

In another aspect, the invention provides methods of reducing the expression of VEGF-C in a cell. Such methods include introducing an isolated nucleic acid molecule in to the cell in an amount sufficient to reduce the expression of VEGF-C. Generally, the nucleic acid molecule has a first portion that is no more than 30 nucleotides in length. The first portion typically includes the sequence 5'-AAG ATC TGG AGG AGC AGT TAC-3' (SEQ ID NO:1), 5'-AAA GGA GGC TGG CAA CAT AAC-3' (SEQ ID NO:2), 5'-AAC CTC CAT GTT GTG TCC GTC-3'(SEQ ID NO:3), 5'-AAG ACC TGC CCC ACC AAT TAC-3' (SEQ ID NO:4), or 5'-AAG AAG TGT GTC GTT GTG TCC-3' (SEQ ID NO:5). According to the invention, the nucleic acid molecule reduces expression of VEGF-C in the cell. VEGF-C expression can be reduced by at least 10%.

The nucleic acid molecules described above also can include a second portion having a sequence complementary to the first portion. Such nucleic acid molecules further can include a linking sequence that joins the first portion and the second portion. For example, the linking sequence can form a loop of a hairpin. Typically, the linking sequence is about 4 to about 10 nucleotides in length, and the first portion is from 19 to 23 nucleotides in length. The invention also provides for vectors containing such nucleic acid molecules, as well as host cells containing such vectors.

A representative cell in which VEGF-C expression can be reduced is a cancer cell. Such cancer cells can be epithelially-derived, and can include, for example, a head and neck cancer cell, a breast cancer cell, a colon cancer cell, and a prostate cancer cell. In various embodiments, the cancer cell is in vivo; the cancer cell is in a mammal (e.g., a human). It is a feature of the invention that proliferation of the cancer cell is inhibited.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DESCRIPTION OF DRAWINGS

Like reference symbols in the various drawings indicate like elements.

DETAILED DESCRIPTION

Figure 1:
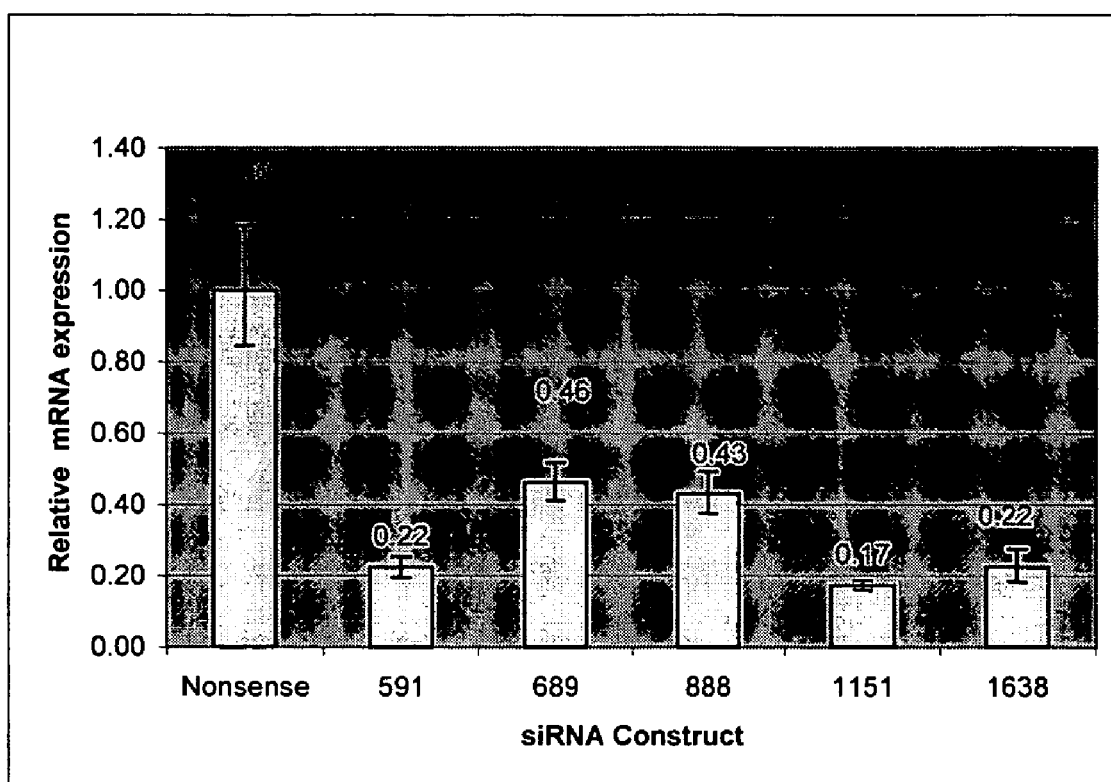
FIG. 1 is a graph showing the results of quantitative RT-PCR of VEGF-C expression in head and neck cancer cells transfected with a VEGF-C siRNA.

Several RNA molecules have been identified that are specific for VEGF-C and that can selectively reduce expression of VEGF-C in a cell. The invention provides for such VEGF-C RNA molecules, the DNA molecules encoding such RNA molecules, and also provides for methods of using the nucleic acid molecules of the invention to reduce the expression of VEGF-C. The RNA molecules of the invention can be used in a number of different forms including antisense, RNAi, and siRNA. Although the following discussion focuses on siRNA, the methods of the invention are not limited by a particular mechanism.

VEGF-C siRNA Molecules

A "small interfering RNA" or "short interfering RNA" or "siRNA" or "short hairpin RNA" or "shRNA" is a double-stranded RNA molecule that is complementary to a target nucleic acid sequence, for example, VEGF-C. A double-stranded RNA molecule is formed by the complementary pairing between a first RNA portion and a second RNA portion. The length of each portion generally is less than 30 nucleotides in length (e.g., 29, 28, 27, 26, 25, 24, 23, 22, 21, 20, 19, 18, 17, 16, 15, 14, 13, 12, 11, or 10 nucleotides). In some embodiments, the length of each portion is 19 to 25 nucleotides in length. In some siRNA molecules, the complementary first and second portions of the RNA molecule are the "stem" of a hairpin structure. The two portions can be joined by a linking sequence, which can form the "loop" in the hairpin structure. The linking sequence can vary in length. In some embodiments, the linking sequence can be 5, 6, 7, 8, 9, 10, 11, 12 or 13 nucleotides in length. A representative linking sequence is 5'-TTC AGA AGG-3', but any of a number of sequences can be used to join the first and second portions. The first and second portions are complementary but may not be completely symmetrical, as the hairpin structure may contain 3' or 5' overhang nucleotides (e.g., a 1, 2, 3, 4, or 5 nucleotide overhang).

RNA molecules have been shown by many researchers to be effective in suppressing mRNA accumulation. siRNA-mediated suppression of nucleic acid expression is specific as even a single base pair mismatch between siRNA and the targeted nucleic acid can abolish the action of RNA interference. siRNAs generally do not elicit anti-viral responses.

There are well-established criteria for designing siRNAs (see, e.g., Elbashire et al., 2001, *Nature*, 411:494–8; Amarzguioui et al., 2004, *Biochem. Biophys. Res. Commun.*, 316(4):1050–8; Reynolds et al., 2004, *Nat. Biotech.*, 22(3): 326-30). Details can be found in the websites of several commercial vendors such as Ambion, Dharmacon, GenScript, and OligoEngine. The sequence of any potential siRNA candidate generally is checked for any possible matches to other nucleic acid sequences or polymorphisms of nucleic acid sequence using the BLAST alignment program (see ncbi.nlm.nih.gov on the World Wide Web). Typically, a number of siRNAs have to be generated and screened in order to compare their effectiveness.

Once designed, the siRNAs of the present invention can be generated by any method known in the art, for example, by in vitro transcription, recombinantly, or by synthetic means (e.g., having either a TT or a UU overhang at the 3' end). siRNAs can be generated in vitro by using a recombinant enzyme, such as T7 RNA polymerase, and DNA oligonucleotide templates, or can be prepared in vivo, for example, in cultured cells (see, for example, Elbashir et al., supra; Brummelkamp et al., supra; and Lee et al., 2002, *Nat. Biotech.*, 20:500–5).

In addition, strategies have been described for producing a hairpin siRNA from vectors containing a RNA polymerase III promoter. Various vectors have been constructed for generating hairpin siRNAs in host cells using either an H1-RNA or an snU6 RNA promoter. A RNA molecule as described above (e.g., a first portion, a linking sequence, and a second portion) can be operably linked to such a promoter. When transcribed by RNA polymerase III, the first and second portions form a duplexed stem of a hairpin and the linking sequence forms a loop. The pSuper vector (OligoEngines Ltd., Seattle, Wash.) also can be used to generate siRNA.

A TTTTT penta-nucleotide usually is attached to the end of the second portion (i.e., the antisense strand) in a vector to serve as a terminator for RNA polymerase III transcription. For that reason, siRNA candidates that contain more than three consecutive Ts should be avoided since four or more consecutive Ts in the template nucleic acid triggers termination of RNA polymerase III transcription.

Several techniques can be used to test the effect of different siRNA constructs on cellular mRNA and/or protein levels. For example, dual-GFP transfection, CHO-cell double transfection based on an antibody/epitope specificity, quantitative RT-PCR, Northern blots, Western blots, immunofluorescence, and Hygro/Neo selection. These methods are well known in the art.

VEGF-C Nucleic Acids and Polypeptides

As used herein, the term "nucleic acid molecule" can include DNA molecules and RNA molecules and analogs of a DNA or RNA molecule generated using nucleotide analogs. A nucleic acid molecule of the invention can be single-stranded or double-stranded, and the strandedness will depend upon its intended use. Fragments or portions of the disclosed nucleotide sequences are also encompassed by the present invention. By "fragment" or "portion" is meant less than full length of the nucleotide sequence.

The invention further encompasses nucleic acid molecules that differ in nucleotide sequence. Nucleic acid molecules that differ in sequence from the original nucleic acid sequence can be generated by standard techniques, such as site-directed mutagenesis, PCR-mediated mutagenesis, or oligonucleotide-mediated mutagenesis. In addition, nucleotide changes can be introduced randomly along all or part of a nucleic acid molecule such as by saturation mutagenesis. Alternatively, nucleotide changes can be introduced into a sequence by chemically synthesizing a nucleic acid molecule having such changes.

To calculate percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It will be appreciated that a single sequence can align differently with other sequences and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

The alignment of two or more sequences to determine percent sequence identity is performed using the algorithm described by Altschul et al. (1997, *Nucleic Acids Res.*, 25:3389–402) as incorporated into BLAST (basic local alignment search tool) programs, available at ncbi.nlm.nih-.gov on the World Wide Web. BLAST searches can be performed to determine percent sequence identity between a nucleic acid molecule of the invention and any other sequence or portion thereof aligned using the Altschul et al. algorithm. BLASTN is the program used to align and compare the identity between nucleic acid sequences, while BLASTP is the program used to align and compare the identity between amino acid sequences. When utilizing BLAST programs to calculate the percent identity between a sequence of the invention and another sequence, the default parameters of the respective programs are used. Sequence analysis of nucleic acid sequences can be performed used BLAST version 2.2.9 (updated on May 12, 2004).

As used herein, an "isolated" nucleic acid molecule is a nucleic acid molecule that is separated from other nucleic acid molecules that are usually associated with the isolated nucleic acid molecule. Thus, an "isolated" nucleic acid molecule includes, without limitation, a nucleic acid molecule that is free of sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector, or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA, or genomic library) or a portion of a gel (e.g., agarose, or polyacrylamine) containing restriction-digested genomic DNA is not to be considered an isolated nucleic acid.

Isolated nucleic acid molecules of the invention can be obtained using techniques routine in the art. For example, isolated nucleic acids within the scope of the invention can be obtained using any method including, without limitation, recombinant nucleic acid technology, and/or the polymerase chain reaction (PCR). General PCR techniques are described, for example in *PCR Primer: A Laboratory Manual*, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid molecule of the invention. Isolated nucleic acids of the invention also can be chemically synthesized, either as a single nucleic acid molecule or as a series of oligonucleotides. In addition, isolated nucleic acid molecules of the invention also can be obtained by mutagenesis using common molecular cloning techniques (e.g., site-directed mutagenesis). Possible mutations include, without limitation, deletions, insertions, substitutions, and combinations thereof.

Vectors containing nucleic acid molecules also are provided by the invention. Vectors, including expression vectors, suitable for use in the present invention are commercially available and/or produced by recombinant DNA technology methods routine in the art. A vector containing a nucleic acid molecule can have elements necessary for expression operably linked to such a nucleic acid, and further can include sequences such as those encoding a selectable marker (e.g., a sequence encoding antibiotic resistance), and/or those that can be used in purification of a polypeptide (e.g., a His tag). A "vector" is defined to include any viral vector, as well as any plasmid, cosmid, phage, or binary vector. Vectors can integrate into the cellular genome or exist extrachromosomally (e.g., an autonomous replicating plasmid with an origin of replication).

Elements necessary for expression include nucleic acid sequences that direct and regulate expression of nucleic acid coding sequences. One example of an element necessary for expression is a promoter sequence. Examples of promoters that may be used in the present invention include the mouse U6 RNA promoters, synthetic human H1RNA promoters, SV40, CMV, RSV, RNA polymerase II, and RNA polymerase III promoters. Elements necessary for expression also can include ribosome-binding sites, introns, enhancer sequences, response elements, or inducible elements that modulate expression of a nucleic acid. Elements necessary for expression can be of bacterial, yeast, insect, mammalian, or viral origin and vectors can contain a combination of elements from different origins. Elements necessary for expression are described, for example, in Goeddel, 1990, *Gene Expression Technology: Methods in Enzymology*, 185, Academic Press, San Diego, Calif. As used herein, operably linked means that a promoter and/or other regulatory element(s) are positioned in a vector relative to a nucleic acid in such a way as to direct or regulate expression of the nucleic acid. A nucleic acid can be operably-linked to regulatory sequences in sense or antisense orientation. For example, in the case of siRNA constructs, expression may refer to the transcription of the siRNA only. In addition, expression can refer to the transcription of sense mRNA and may also refer to the production of protein.

In one embodiment of the present invention, a vector contains an H1-RNA promoter that is operably linked to a nucleic acid sequence encoding a siRNA. Thus, the H1-RNA promoter initiates the transcription of the siRNA. In another embodiment, the promoter is regulatable, providing inducible expression of the siRNA.

Another aspect of the invention pertains to host cells into which a vector of the invention, e.g., an expression vector, or an isolated nucleic acid molecule of the invention has been introduced. The term "host cell" refers not only to the particular cell but also to the progeny or potential progeny of such a cell. A host cell can be any prokaryotic or eukaryotic cell. For example, host cells can include bacterial cells such as *E. coli*, insect cells, yeast cells, or mammalian cells (such as Chinese hamster ovary cells (CHO) or COS cells). Other suitable host cells are known to those skilled in the art. Many methods for introducing nucleic acids into host cells, both in vivo and in vitro, are well known to those skilled in the art and include, without limitation, calcium phosphate precipitation, electroporation, heat shock, lipofection, microinjection, and viral-mediated nucleic acid transfer.

A "polypeptide" refers to a polypeptide encoded by a nucleic acid molecule. The term "purified" polypeptide as used herein refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified."

Polypeptides can be purified from natural sources (e.g., a biological sample) by known methods such as DEAE ion exchange, gel filtration, and hydroxyapatite chromatography. A purified polypeptide also can be obtained by expressing a nucleic acid in an expression vector, for example. In addition, a purified polypeptide can be obtained by chemical synthesis. The extent of purity of a polypeptide can be measured using any appropriate method, e.g., column chromatography, polyacrylamide gel electrophoresis, or HPLC analysis.

In addition to naturally-occurring polypeptides, the skilled artisan will further appreciate that changes can be introduced into a nucleic acid molecule as discussed herein, thereby leading to changes in the amino acid sequence of the encoded polypeptide. For example, changes can be introduced into a nucleic acid coding sequence leading to conservative and/or non-conservative amino acid substitutions at one or more amino acid residues. A "conservative amino acid substitution" is one in which one amino acid residue is replaced with a different amino acid residue having a similar side chain. Similarity between amino acid residues has been assessed in the art. For example, Dayhoff et al. (1978, in *Atlas of protein Sequence and Structure*, Vol. 5, Suppl. 3, pp 345–352) provides frequency tables for amino acid substitutions that can be employed as a measure of amino acid similarity. A non-conservative substitution is one in which an amino acid residue is replaced with an amino acid residue that does not have a similar side chain.

The invention also provides for chimeric or fusion polypeptides. As used herein, a "chimeric" or "fusion" polypeptide includes one polypeptide operatively linked to a heterologous polypeptide. The heterologous polypeptide can be at either the N-terminus or C-terminus of the polypeptide. Within a chimeric or fusion polypeptide, the term "operatively linked" is intended to indicate that the two polypeptides are encoded in-frame relative to one another. In a fusion polypeptide, the heterologous polypeptide generally has a desired property such as the ability to purify the fusion polypeptide (e.g., by affinity purification). A chimeric or fusion polypeptide of the invention can be produced by standard recombinant DNA techniques, and can use commercially available vectors.

A polypeptide commonly used in a fusion polypeptide for purification is glutathione S-transferase (GST), although numerous other polypeptides are available and can be used. In addition, a proteolytic cleavage site can be introduced at the junction between a polypeptide and a heterologous polypeptide to enable separation of the two polypeptides subsequent to purification of the fusion polypeptide. Enzymes that cleave such proteolytic sites include Factor Xa, thrombin, or enterokinase. Representative expression vectors encoding a heterologous polypeptide that can be used in affinity purification of a polypeptide include pGEX (Pharmacia Biotech Inc; Smith & Johnson, 1988, *Gene*, 67:31–40), pMAL (New England Biolabs, Beverly, Mass.) and pRIT5 (Pharmacia, Piscataway, N.J.).

Detection of Nucleic Acids and Polypeptides

Nucleic acid molecules and polypeptides can be detected using a number of different methods. Methods for detecting nucleic acids include, for example, PCR and nucleic acid hybridizations (e.g., Southern blot, Northern blot, or in situ hybridizations). Specifically, oligonucleotides (e.g., oligonucleotide primers) capable of amplifying a target nucleic acid can be used in a PCR reaction. PCR methods generally include the steps of obtaining a sample, isolating nucleic acid (e.g., DNA, RNA, or both) from the sample, and contacting the nucleic acid with one or more oligonucleotide primers that hybridize(s) with specificity to the template nucleic acid under conditions such that amplification of the template nucleic acid occurs. In the presence of a template nucleic acid, an amplification product is produced. Conditions for amplification of a nucleic acid and detection of an amplification product are known to those of skill in the art (see, e.g., *PCR Primer: A Laboratory Manual*, 1995, Dieffenbach & Dveksler, Eds., Cold Spring Harbor Laboratory Press, Cold Spring Harbor, N.Y.; and U.S. Pat. Nos. 4,683,195; 4,683,202; 4,800,159; and 4,965,188). Modifications to the original PCR also have been developed. For example, anchor PCR, RACE PCR, RT-PCR, or ligation chain reaction (LCR) are additional PCR methods known in the art (see, e.g., Landegran et al., 1988, *Science*, 241:1077–1080; and Nakazawa et al., 1994, *Proc. Natl. Acad. Sci. USA*, 91:360–364).

As used herein, "standard amplification conditions" refer to the basic components of an amplification reaction mix, and cycling conditions that include multiple cycles of denaturing the template nucleic acid, annealing the oligonucleotide primers to the template nucleic acid, and extension of the primers by the polymerase to produce an amplification product (see, for example, U.S. Pat. Nos. 4,683,195; 4,683,202; 4,800,159; and 4,965,188). The basic components of an amplification reaction mix generally include, for example, about 10–25 nmole of each of the four deoxynucleoside triphosphates, (e.g., dATP, dCTP, dTTP, and dGTP, or analogs thereof), 10–100 pmol of each primer, template nucleic acid, and a polymerase enzyme. The reaction components are generally suspended in a buffered aqueous solution having a pH of between about 7 and about 9. The aqueous buffer can further include one or more co-factors (e.g., $Mg^{2+}$, $K^+$) required by the polymerase. Additional components such as DMSO are optional. Template nucleic acid is typically denatured at a temperature of at least about 90° C., and extension from primers is typically performed at a temperature of at least about 72° C.

The annealing temperature can be used to control the specificity of amplification. The temperature at which primers anneal to template nucleic acid must be below the Tm of each of the primers, but high enough to avoid non-specific annealing of primers to the template nucleic acid. The Tm is the temperature at which half of the DNA duplexes have separated into single strands, and can be predicted for an oligonucleotide primer using the formula provided in section 11.46 of Sambrook et al. (1989, *Molecular Cloning: A Laboratory Manual*, 2nd Ed., Cold Spring Harbor Laboratory Press, Cold Spring Harbor, N.Y.). Non-specific amplification products are detected as bands on a gel that are not the size expected for the correct amplification product. It can be appreciated by those of skill in the art that appropriate positive and negative controls should be performed with every set of amplification reactions to avoid uncertainties related to contamination and/or non-specific annealing of oligonucleotide primers and extension therefrom.

A pair of primers in an amplification reaction must anneal to opposite strands of the template nucleic acid, and should be an appropriate distance from one another such that the polymerase can effectively polymerize across the region and such that the amplification product can be readily detected using, for example, electrophoresis. Oligonucleotide primers can be designed using, for example, a computer program such as OLIGO (Molecular Biology Insights Inc., Cascade, Colo.) to assist in designing primers that have similar melting temperatures. Typically, oligonucleotide primers are 10 to 30 or 40 or 50 nucleotides in length (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length), but can be longer or shorter if appropriate amplification conditions are used. Oligonucleotides of the invention can be obtained by restriction enzyme digestion of a nucleic acid molecule or can be prepared by standard chemical synthesis and other known techniques.

Alternatively, a nucleic acid can be detected using a labeled oligonucleotide probe capable of hybridizing to nucleic acids on a Southern blot. In the presence of homologous nucleic acid, a hybridization complex is produced between the nucleic acid and the oligonucleotide probe. Hybridization between nucleic acid molecules is discussed in detail in Sambrook et al. (1989, *Molecular Cloning: A Laboratory Manual*, $2^{nd}$ Ed., Cold Spring Harbor Laboratory Press, Cold Spring Harbor, N.Y.; Sections 7.37–7.57, 9.47–9.57, 11.7–11.8, and 11.45–11.57).

For oligonucleotide probes less than about 100 nucleotides, Sambrook et al. discloses suitable Southern blot conditions in Sections 11.45–11.46. The Tm between a sequence that is less than 100 nucleotides in length and a second sequence can be calculated using the formula provided in Section 11.46. Sambrook et al. additionally discloses prehybridization and hybridization conditions for a Southern blot that uses oligonucleotide probes greater than about 100 nucleotides (see Sections 9.47–9.52). Hybridizations with an oligonucleotide greater than 100 nucleotides generally are performed 15–25° C. below the Tm. The Tm between a sequence greater than 100 nucleotides in length and a second sequence can be calculated using the formula provided in Sections 9.50–9.51 of Sambrook et al. Additionally, Sambrook et al. recommends the conditions indicated in Section 9.54 for washing a Southern blot that has been probed with an oligonucleotide greater than about 100 nucleotides.

The conditions under which membranes containing nucleic acids are prehybridized and hybridized, as well as the conditions under which membranes containing nucleic acids are washed to remove excess and non-specifically bound probe can play a significant role in the stringency of the hybridization. Such hybridizations can be performed, where appropriate, under moderate or high stringency conditions. Such conditions are described, for example, in Sambrook et al. section 11.45–11.46. For example, washing conditions can be made more stringent by decreasing the salt concentration in the wash solutions and/or by increasing the temperature at which the washes are performed. In addition, interpreting the amount of hybridization can be affected, for example, by the specific activity of the labeled oligonucleotide probe, by the number of probe-binding sites on the template nucleic acid to which the probe has hybridized, and by the amount of exposure of an autoradiograph or other detection medium.

It will be readily appreciated by those of ordinary skill in the art that although any number of hybridization and washing conditions can be used to examine hybridization of a probe nucleic acid molecule to immobilized target nucleic acids, it is more important to examine hybridization of a probe to target nucleic acids under identical hybridization, washing, and exposure conditions. Preferably, the target nucleic acids are on the same membrane.

A nucleic acid molecule is deemed to hybridize to a target nucleic acid but not to a non-homologous nucleic acid if hybridization to the homologous target nucleic acid is at least 5-fold (e.g., at least 6-fold, 7-fold, 8-fold, 9-fold, 10-fold, 20-fold, 50-fold, or 100-fold) greater than hybridization to the non-homologous nucleic acid. The amount of hybridization can be quantitated directly on a membrane or from an autoradiograph using, for example, a Phosphorimager or a Densitometer (Molecular Dynamics, Sunnyvale, Calif.).

Detection of an amplification product or a hybridization complex is usually accomplished using detectable labels. The term "label" with regard to a nucleic acid is intended to encompass direct labeling of a nucleic acid by coupling (i.e., physically linking) a detectable substance to the nucleic acid, as well as indirect labeling of the nucleic acid by reactivity with another reagent that is directly labeled with a detectable substance. Detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$. An example of indirect labeling includes end-labeling a nucleic acid with biotin such that it can be detected with fluorescently labeled streptavidin.

Therapeutic Uses of VEGF-C RNA Molecules

According to the methods of the invention, the expression of VEGF-C can be reduced by introducing a VEGF-C nucleic acid molecule of the invention into a cell. For example, the expression of VEGF-C can be reduced in a cancer cell or any other cell in which a reduction in VEGF-C is desirable. A reduction in expression of VEGF-C can be due to a reduction in the amount of VEGF-C mRNA and/or the encoded polypeptide, and is reduced compared to expression in the absence of the nucleic acid molecule. The term "reduced" is used herein to indicate that expression of VEGF-C is reduced by 1–100% (e.g., 10%, 20%, 30%, 40%, 50%, 60%, 70%, 80%, 90%, 95%, or 99% reduced). "Knock-down" or "knock-down technology" refers to techniques in which the expression of a target nucleic acid is reduced compared to expression of the target nucleic acid in the absence of a RNA molecule.

The term "VEGF-C" is meant to refer to an enzyme that is a member of the vascular endothelial growth factor family, and is involved in angiogenesis. "VEGF-C" also refers to the nucleic acid (DNA or RNA) encoding such an enzyme. Representative sequences of VEGF-C can be found, for example, without limitation, in GenBank Accession Nos. NM_053653 and AY032729 (*Rattus norvegicus*), AF009178 (*Bos taurus*), NM_005429 and X94216 (*Homo sapiens*), NM_009506 and U73620 (*Mus musculus*), and Y15837 (*Coturnix coturnix*).

For example, the expression of VEGF-C mRNA can be reduced in a cell by antisense, RNAi, or siRNA. A siRNA can be two separate RNA molecules that hybridize together, or a single molecule that forms a hairpin.

The VEGF-C nucleic acid molecules of the invention can be used to reduce the expression of VEGF-C in a number of cell types or tissue types. For example, the VEGF-C nucleic acid molecules of the invention can be used to reduce the expression of VEGF-C in cancer cells. As used herein, "cancer cells" refer to cells that grow uncontrollably and/or abnormally, and can be, for example, epithelial carcinomas. Epithelial carcinomas include, for example, head and neck cancer cells, breast cancer cells, prostate cancer cells, and colon cancer cells. The nucleic acid molecules of the invention are preferably administered so as to result in an inhibition of the proliferation of cancer cells. Proliferation of cancer cells as used herein refers to an increase in the number of cancer cells (in vitro or in vivo) over a given period of time (e.g., hours, days, weeks, or months). It is noted that the number of cancer cells is not static and reflects both the number of cells undergoing cell division and the number of cells dying (e.g., by apoptosis). An inhibition of the proliferation of cancer cells can be defined as a decrease in the rate of increase in cancer cell number, a complete loss of cancer cells, or any variation therebetween. With respect to tumors, a decrease in the size of a tumor can be an indication of an inhibition of proliferation.

The amount of a nucleic acid molecule administered will vary depending on various factors including, but not limited to, the composition chosen, the particular type and stage of cancer, the weight, the physical condition, and the age of the individual, and whether prevention or treatment is to be achieved. Such factors can be readily determined by a clinician using animal models or other test systems that are well known in the art. The nucleic acids of the present invention can be delivered to a cell in a number of ways. For example, a nucleic acid molecule of the invention (e.g., a siRNA) can be directly administered to a cell, or a vector encoding a nucleic acid molecule of the invention (e.g., a viral vector) can be administered to a cell. Viral vectors include, without limitation, a lentivirus, an adenovirus, an adeno-associated virus, a retrovirus, a vaccinia virus, a herpes viruses, and a bovine papilloma virus. In addition, a nucleic acid molecule of the invention or a vector encoding such a nucleic acid can be encapsulated in, for example, a nanoparticle or a liposome, and administered to a cell.

A pharmaceutical composition of the invention is formulated to be compatible with its intended route of administration. For example, the therapeutic agent may be introduced directly into the cancer of interest via direct injection. Additionally, examples of routes of administration include parenteral, e.g., intravenous, intradermal, subcutaneous, oral (e.g., ingestion or inhalation), transdermal (topical), transmucosal, and rectal administration. siRNA molecules of the invention can be incorporated into pharmaceutical compositions suitable for administration. Such compositions typically comprise the nucleic acid molecule, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art.

Solutions or suspensions can include the following components: a sterile diluent such as water for injection, saline solution (e.g., phosphate buffered saline (PBS)), fixed oils, a polyol (for example, glycerol, propylene glycol, and liquid polyetheylene glycol, and the like), glycerine, or other synthetic solvents; antibacterial and antifungal agents such as parabens, chlorobutanol, phenol, ascorbic acid, thimerosal, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol or sorbitol, and sodium chloride in the composition. Prolonged administration of the injectable compositions can be brought about by including an agent that delays absorption. Such agents include, for example, aluminum monostearate and gelatin. The parenteral preparation can be enclosed in ampules, disposable syringes, or multiple dose vials made of glass or plastic.

Oral compositions generally include an inert diluent or an edible carrier. Oral compositions can be liquid, or can be enclosed in gelatin capsules or compressed into tablets. Pharmaceutically compatible binding agents, and/or adjuvant materials can be included as part of an oral composition. Tablets, pills, capsules, troches and the like can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. Transmucosal administration can be accomplished through the use of nasal sprays or suppositories. For transdermal administration, the active compounds are formulated into ointments, salves, gels, or creams as generally known in the art.

It is especially advantageous to formulate compositions in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms of the invention are dependent upon the amount of a compound necessary to inhibit proliferation of the cancer cells. The amount of a compound necessary to inhibit proliferation of the cancer cells can be formulated in a single dose, or can be formulated in multiple dosage units. Treatment may require a one-time dose, or may require repeated doses.

Articles of Manufacture

The invention encompasses articles of manufacture (e.g., kits) that contain one or more nucleic acid molecules of the invention, or one or more vectors that encode a nucleic acid molecule of the invention. Such nucleic acid molecules are formulated for administration as described herein, and are packaged appropriately for the intended route of administration. For example, a nucleic acid molecule of the invention or a vector encoding a nucleic acid molecule of the invention can be contained within a pharmaceutically acceptable carrier.

Kits of the invention also can include additional reagents (e.g., buffers, co-factors, or enzymes). Pharmaceutical compositions of the invention further can include instructions for administering the composition to an individual. The kit also can contain a control sample or a series of control samples that can be assayed and compared to the biological sample. Each component of the kit is usually enclosed within an individual container and all of the various containers are within a single package.

The invention will be further described in the following examples, which do not limit the scope of the invention described in the claims.

EXAMPLES

Example 1 siRNA Design Cloning and DNA Preparation

Target identification and Oligonucleotide Design

Five VEGF-C siRNA sequences were screened for ability to reduce VEGF-C mRNA levels using quantitative RT-PCR. The five siRNA molecules were distributed along the VEGF-C coding sequence. The following strategy was used for designing the VEGF-C siRNA molecules.

At the NCBI website (ncbi.nlm.nih.gov on the World Wide Web), the FASTA version of the VEGF-C sequence was selected and imported into the siRNA Finder program at Ambion's website (ambion.com/techlib/misc/siRNA_finder on the World Wide Web). The following parameters were then selected: siRNA's to end with TT; no more than 50% GC content; and no polyA or polyT sequences (no more than 4 consecutive). The VEGF-C sequence was submitted for processing. The program is able to format the oligonucleotide sequences such that they are suitable for a particular pSilencer vector. The program designs oligonucleotides to include a leader sequence with the correct restriction site for the chosen vector, the sense sequence of the target sequence, a 9-nt hairpin (TTCAAGAGA), an antisense of the target sequence, RNA polymerase III termination sequence (poly T), and a restriction site at the 3' end for cloning. Unless otherwise indicated, the pSilencer vector designated 2.1-U6 was used in the experiments described herein. The oligonucleotide sequences identified by the program were ordered from Sigma/Genosys (The Woodlands, Tex.) on a 50 nM scale with standard desalting purification. Each construct for each target position contained 2 oligonucleotides (a sense and an anti-sense strand) each around 63 to 64 nucleotides in length.

Annealing the Oligonucleotide

Each oligonucleotide was diluted with QS PCR-grade water to 1 µg/µL using the $OD_{260}$ reading reported from the manufacturer. The oligonucleotide suspension was vortexed and centrifuged. 2 µL siRNA oligonucleotide (sense), 2 µL siRNA oligonucleotide (antisense), and 46 µL annealing buffer (100 mM NaCl+50 mM HEPES (pH 7.4)) were combined and heated to 95° C. for 1 h in a PCR machine. The tubes were then centrifuged, placed in a 37° C. water bath for 1 to 2 hours, and cooled to room temperature. Oligonucleotides were stored at −20° C.

Vector Ligation

Vector ligation was optimized for the pSilencer 2.1-U6 system (Ambion; Austin, Tex.). 5 µL of annealed siRNA oligonucleotides were diluted by the addition of 45 µL PCR-grade water. The ligation reaction included 6 µL nuclease-free water, 1 µL 10× T4 DNA ligase buffer, 1 µL pSilencer 2.1 U6 Hygro/Neo vector, 1 µL (~400 U) T4 DNA ligase (New England Biolabs), and 1 µL of the diluted and annealed siRNA oligonucleotides described above. The ligation reaction was either incubated for 30 minutes at 37° C. or for 3–12 hours at room temperature. The ligated vectors were stored at −20° C.

Bacterial Transformation and Plating

Tubes of ONE SHOT® competent *E. coli* cells (Invitrogen) were thawed on ice. Five µL of ligated siRNA vector was added to the competent cells and mixed by gently flicking the tube. The mixture was incubated on ice for 30 minutes, heat-shocked for 45 sec at 42° C., and returned immediately to the ice for about five minutes. 250 µL SOC media (provided by the manufacturer with the competent cells) was added to the mixture, and the mixture was shaken vigorously at 37° C. for 1 to 2 h. 50 and 250 µL of SOC bacterial broth was plated onto individual LB-Amp+plates (50–100 µg/mL, pre-warmed to 37° C.) using sterile spreading techniques. The plates were incubated at 37° C. for 12–14 hours.

Mini-PREPS

Five mini preps were prepared for each VEGF-C siRNA construct. Three to four ml of LB-Amp+broth were added to each 15 ml tube. Individual colonies were picked from the overnight plates using a sterile 200 µL pipette tip. The pipette tip was usually ejected directly into the tube. The tubes were shaken vigorously for 12 to 14 h at 37° C. using a Domann incubator. One to 3 ml of broth was removed and centrifuged in 1.5 ml eppendorf tubes to pellet the bacteria. The remaining vials and broth were stored at 4° C. Minipreps were performed according to the Qiagen protocol, except that the DNA was eluted using water and not the elution buffer supplied by the manufacturer.

One to 2 µL of eluted DNA resuspended in 5 to 6 µL water (final volume of 7 µL) was submitted to the University of Iowa DNA Facility for sequencing. Sequencing reactions of the pSilencer 1.0-U6 vector and the pSilencer 2.1-U6 Hygro vector used the T7 core primer, and sequencing reactions of the pSilencer 2.1-U6 Neo vector used the M13 core primer. Intact siRNA sequence insertions were confirmed by comparing the sequence results with the oligonucleotides designed using the siRNA Finder computer program.

Maxi-PREPS and Glycerol Stock Preparation

Once a correctly cloned insert and vector were identified, the remaining 1–2 ml of the original overnight culture was used to inoculate 100 ml of LB-Amp+ in a sterile 500 ml Erlenmeyer flask. The inoculated media was shaken vigorously at ≧200 rpms at 37° C. for 12–14 h. A glycerol stock was made of each vector using 1.5 ml of bacterial broth and 0.5 ml of sterile 60% glycerol. The remaining broth was ultracentrifuged at 6000 rpm for 15 minutes to pellet the bacteria, and the supernatant was removed. DNA was extracted using the Qiagen Filter Maxi-prep technique. The amount of DNA obtained was measured using $OD_{260}/OD_{280}$, and samples were frozen at −20° C.

Example 2 siRNA Testing and GFP Sorting

Dual-GFP transfection was used to test the effect of different siRNA constructs on cellular mRNA and/or protein levels. The dual-GFP transfection technique is the process of double-transfecting siRNA expression vectors with a large excess of a GFP expression vector. Following 24–48 hours, the cells were sorted on a flow cytometer, and GFP-positive cells were collected.

Cell Culture and DNA Transfection 1.0 to 1.5×10$^6$ UM-SCC-1 cells from each construct were seeded in duplicate onto 100 mm tissue culture plates. Twenty-four hours later, cells had reached about 50–70% confluency. DNA was transfected using Qiagen's Effectene® kit. Toxicity was reduced with high quality and high purity DNA. For transfections, a ratio of 1:3 or 1:4 (GFP: construct) generally was used (e.g., 1 µg of GFP vector DNA (pEGFP-N1 vector), and 3–4 µg of construct DNA), however, a ratio of up to 1:7 also was used successfully. Preliminary experiments determined that a 1:8:10 ratio of DNA: enhancer: effectene (1 µg of DNA, 8 µL of enhancer, and 10 µL of effectene) resulted in efficient transfection.

General transfection techniques for a single sample are described. The DNA (3 µg construct and 1 µg GFP per sample) was diluted into 300 µL EC buffer (provided with kit) in a 15 mL Falcon tube. Prior to beginning transfection, media was removed from plates, the plates were washed once with PBS, and 7 mL of complete media (+ABX and serum) was added to each plate. 32 TL of enhancer was added and the mixture was vortexed for 1 sec and then incubated for five minutes at room temperature. 40 µL of effectene was added and the mixture was vortexed for 10 sec and then incubated at room temperature for five minutes. Three mL of complete media was added to the mixture, the tube was inverted to mix, and the media was added dropwise to the plates. Approximately 20–30% transfection efficiency was observed with UM-SCC-1 cells.

Complexes were removed after 4–6 hours. Plates were washed one time with PBS and refreshed with complete media. The complexes were incubated for 24–120 hours before sorting. Plates were checked daily for signs of toxicity.

Sorting

Plates were trypsinized approximately one hour in advance of sorting, and duplicate samples were combined into a single tube. Cells were pelleted, and resuspended in 1 mL of PBS. Cells were filtered using a 70μ filter, and the filtrate was transferred into flow tubes. A 15 mL Falcons tube containing 2 to 3 mL of complete media was prepared for each sample. The samples and the sorting tubes were transported to the flow lab for sorting.

Sample Preparation

The number of cells collected was noted for each sample. The number of cells collected represents the GFP$^+$cells, which, by association, should contain a large amount of siRNA vector. To measure RNA transcripts, 100,000 cells or more (e.g., 250,000 cells) were collected. To measure polypeptides, 250,000 cells or more (e.g., 500,000 cells) were collected.

To examine the level of RNA transcripts, the collected cells were pelleted, the supernatant was removed, and the cells were resuspended in 333 μL of Trizol (Gibco BRL, Carlsbad, Calif.). The resuspended cells were stored at −80° C. for no more than 1 week before the RNA was extracted. Taqman RT-PCR was used to assay for the level of mRNA expression in the cells. Reduced levels of mRNA expression generally were observed by 24 to 48 hours after sorting.

To examine the level of polypeptide, the collected cells were pelleted, the supernatant was removed, and the cells were resuspended in 1 mL PBS. The cells were again pelleted, the supernatant removed, and 40 to 50 μL of lysis buffer was added. The cells were heated to boiling for seven minutes, and if necessary, stored at −20° C. A Bradford assay and Western blotting can be used to assay for the level of polypeptide in the cells. Reduced levels of polypeptides generally were observed for up to 70 to 120 hours after sorting.

Example 3

VEGF-C siRNA Sequences and Results

The VEGF-C siRNAs were designated as described in Example 1. The VEGF-C siRNA sequences are shown in Table 1.

TABLE 1

| Position relative to VEGF-C sequence[a] | 5'→3' Sequence | SEQ ID NO: |
|---|---|---|
| 591–611 | AAGATCTGGAGGAGCAGTTAC | 1 |
| 689–709 | AAAGGAGGCTGGCAACATAAC | 2 |
| 888–908 | AACCTCCATGTTGTGTCCGTC | 3 |
| 1151–1171 | AAGACCTGCCCCACCAATTAC | 4 |
| 1638–1658 | AAGAAGTGTGTCGTTGTGTCC | 5 |

[a]GenBank Accession No. NM_005429

Double-transfected UM-SCC-1 cells were sorted for GFP expression followed by RNA extraction and/or protein extraction and PCR or Western blot. Each oligonucleotide sequence was screened in direct comparison to a scrambled control RNA molecule that does not target any known human gene but does initiate the RNAi cascade. FIG. 1 shows the results of a representative experiment with the data presented as the percent of control mRNA levels. The five VEGF-C siRNA molecules designed reduced the accumulation of VEGF-C in cells by about 54% to about 83%.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule comprising a nucleic acid sequence that is no more than 30 nucleotides in length that comprises 5'-AAG ACC TGC CCC ACC AAT TAC-3' (SEQ ID NO:4).

2. The nucleic acid molecule of claim 1, further comprising a second nucleic acid sequence that is no more than 30 nucleotides in length that is complementary to the nucleic acid sequence that comprises SEQ ID NO:4.

3. The nucleic acid molecule of claim 2, further comprising a linking sequence that joins the nucleic acid sequence that comprises SEQ ID NO:4 with the second nucleic acid sequence.

4. The nucleic acid molecule of claim 3, wherein the linking sequence forms a loop of a hairpin.

5. The nucleic acid molecule of claim 4, wherein the linking sequence is about 4 to about 10 nucleotides in length.

6. The nucleic acid molecule of claim 1, wherein the sequence that comprises SEQ ID NO:4 is from 21 to about 23 nucleotides in length.

7. A vector comprising the nucleic acid molecule of claim 1.

8. An isolated host cell comprising the vector of claim 7.

9. A method of reducing the expression of VEGF-C in a cell in vitro, comprising the step of introducing the isolated nucleic acid molecule of claim 1 or the vector of claim 7 into the cell in vitro in an amount sufficient to reduce the expression of VEGF-C in the cell.

10. The method of claim 9, wherein expression of VEGF-C is reduced by at least 10%.

11. The method of claim 9, wherein the cell is a cancer cell.

12. The method of claim 11, wherein the cancer cell is an epithelially-derived cancer cell.

13. The method of claim 12, wherein the epithelially-derived cancer cell is a head and neck cancer cell, a breast cancer cell, a colon cancer cell, or a prostate cancer cell.

14. The method of claim 11, wherein the cancer cell is a mammalian cancer cell.

15. The method of claim 14, wherein the mammalian cancer cell is a human cancer cell.

16. The method of claim 11, wherein proliferation of the cancer cell is inhibited.

17. A composition comprising the isolated nucleic acid molecule of claim 1 or the vector of claim 7.

18. The composition of claim 17, further comprising a pharmaceutically acceptable carrier.

19. A composition comprising the isolated host cell of claim 8.

* * * * *